US008306179B2

(12) United States Patent
Anashkin et al.

(10) Patent No.: US 8,306,179 B2
(45) Date of Patent: Nov. 6, 2012

(54) RECONSTRUCTION OF LINEARLY MOVING OBJECTS WITH INTERMITTEN X-RAY SOURCES

(75) Inventors: Edward Anashkin, San Diego, CA (US); Irving Weinberg, Bethesda, MD (US)

(73) Assignee: Weinberg Medical Physics LLC, Bethesda, MD (US)

( * ) Notice: Subject to any disclaimer, the term of this patent is extended or adjusted under 35 U.S.C. 154(b) by 0 days.

(21) Appl. No.: 13/016,064

(22) Filed: Jan. 28, 2011

(65) Prior Publication Data
US 2011/0182401 A1    Jul. 28, 2011

Related U.S. Application Data

(60) Provisional application No. 61/299,181, filed on Jan. 28, 2010.

(51) Int. Cl.
*A61B 6/00*    (2006.01)
(52) U.S. Cl. ............................................. 378/4; 378/19
(58) Field of Classification Search ................ 378/4, 21, 378/26
See application file for complete search history.

(56) References Cited

U.S. PATENT DOCUMENTS

| | | | |
|---|---|---|---|
| 2,000,497 A | 5/1935 | Pohl | |
| 3,178,575 A | 4/1965 | Koerner | |
| 4,903,204 A * | 2/1990 | Dobbins, III | 382/255 |
| 5,023,895 A | 6/1991 | McCroskey et al. | |
| 5,469,486 A | 11/1995 | Hu et al. | |
| 5,901,198 A | 5/1999 | Crawford et al. | |
| 6,226,350 B1 * | 5/2001 | Hsieh | 378/98 |
| 6,256,370 B1 * | 7/2001 | Yavuz | 378/22 |
| 6,320,929 B1 | 11/2001 | van Der Haar | |
| 6,823,044 B2 * | 11/2004 | Rosner | 378/98.8 |
| 7,110,497 B2 * | 9/2006 | Halsmer et al. | 378/98.12 |
| 8,098,795 B2 * | 1/2012 | Nowak et al. | 378/98.8 |
| 2005/0002550 A1 * | 1/2005 | Jabri et al. | 382/131 |
| 2005/0226375 A1 * | 10/2005 | Eberhard et al. | 378/62 |
| 2005/0265590 A1 * | 12/2005 | Li et al. | 382/131 |
| 2006/0182224 A1 | 8/2006 | Besson | |
| 2006/0185165 A1 | 8/2006 | Vafi et al. | |
| 2008/0108895 A1 | 5/2008 | Sabol et al. | |
| 2008/0273651 A1 | 11/2008 | Boas | |
| 2008/0285712 A1 | 11/2008 | Kopans et al. | |

OTHER PUBLICATIONS

Dobbins, III et al., Digital x-ray tomosynthesis: current stae of the art and clinical potential, Phys Med Biol, 48, 2003, pp. R65-R106.*
Claus et al., A new method for 3D reconstruction in digital tomosynthesis, Medical Imaging, Proceedings of SPIE, vol. 4684, 2002, pp. 814-824.*
International Search Report for International Application No. PCT/US2011/22927, dated Jan. 28, 2011.

(Continued)

*Primary Examiner* — Alexander H Taningco
(74) *Attorney, Agent, or Firm* — Barnes & Thornburg LLP

(57) ABSTRACT

A method and apparatus for performing computed tomography in medical imaging through reconstruction of a data set containing projections obtained during relative motions a container or body of interest with respect to an x-ray source and/or x-ray detector panel. Strobing of the data is implemented through one or more methods to include pulsing of the x-ray source, intermittent blanking of the x-ray detector panel, or intermittent processing of data collected from the detector panel to simulate blanking. The invention is utilized to significantly improve contrast by taking advantage of the pulsed nature of the source to implement three-dimensional reconstruction.

13 Claims, 7 Drawing Sheets

OTHER PUBLICATIONS

Written Opinion of the International Searching Authority for International Patent Application No. PCT/US2011/22927 mailed Apr. 7, 2011.

Matsuo et al., "Three-Dimensional Image Reconstruction by Digital Tomo-Synthesis Using Inverse Filtering", IEEE Transactions on Medical Imaging, vol. 12, No. 2, (1993), pp. 307-313.

Moore et al., "Three-Dimensional X-Ray Laminography As a Tool for Detection and Characterization of BGA Package Defects", IEEE Transactions on Components and Packaging Technologies, vol. 25, No. 2, (2002), pp. 224-229.

Cao et al., "A Dynamic Micro-CT Scanner Based on a Carbon Nanotube Field Emission X-Ray Source", Physics in Medicine and Biology, vol. 54, (2009) pp. 2323-2340.

Raskar et al., "Coded Exposure Photography: Motion Deblurring Using Fluttered Shutter", Mitsubishi Electric Research Labs, 2006.

\* cited by examiner

PHANTOM B

RECONSTRUCTION OF LINEARLY MOVING OBJECTS WITH INTERMITTEN X-RAY SOURCES

FIELD OF THE INVENTION

The present invention concerns an apparatus and a method that perform an image reconstruction technique that takes advantage of an object's relative linear translation between an intermittent source and one or more x-ray detector panels.

BACKGROUND OF THE INVENTION

Computed tomography has long been used to increases conspicuity of low-contrast objects in medical imaging, by reducing the effect of overlapping structures. Portal imaging of trucks and containers for homeland security could potentially benefit from a similar ability.

For medical applications, computed tomography is generally achieved through reconstruction of a data set containing projections obtained at angles on all sides of a container or body of interest. The ability to entirely encircle a body of interest is not always possible in the clinic, and can be challenging in certain portal inspection applications (e.g., trucks).

Two-dimensional x-ray imaging systems have been implemented for inspection of trucks and baggage, sometimes with pulsed x-ray sources. Likewise, transmission x-ray imaging is widely used for medical, security, and commercial applications in the form of two-dimensional (2D) projection (conventional X-ray) or three-dimensional (3D) Computed Tomography (CT). In CT scanning, digital image reconstruction is used to generate a three-dimensional image of the inside of an object from a complete angular series of two-dimensional x-ray images taken around a single axis of rotation. Such information about the three-dimensional structure of an object can be valuable; however in some cases it is not easy to entirely surround an object with sources and detectors, especially if the object is in motion.

Classically, radiologists have reduced the influence of overlapping structures in a three-dimensional object by counter-rotating the x-ray source and x-ray detector in parallel planes ("laminography"). This results in a "smearing" of the images of objects of interest in planes other than the focal plane into a uniform background as disclosed in T. D. Moore, D. Vanderstraeten, P. M. Forssell, *Three-Dimensional X-Ray Laminography as a Tool for Detection and Characterization of BGA Package Defects*, IEEE Transactions on Components and Packaging Technologies, 25(2):224-229 (2002) (hereby incorporated by reference in its entirety). The smearing can be applied with analog means (i.e., with film) or via digital tomosynthesis as disclosed in H. Matsuo, A. Iwata, I. Horiba, N. Suzumura, *Three-Dimensional Image Reconstruction by Digital Tomo-Synthesis Using Inverse Filtering*, IEEE Transactions on Medical Imaging, 12(2):307-313 (1993) (hereby incorporated by reference in its entirety). The counter-rotating process requires sequential refocusing to examine multiple planes, and can be difficult to apply to objects in linear motion with respect to the source/detector pairs.

SUMMARY

Disclosed embodiments provide an appropriate reconstruction technique that takes advantage of an object's translation between a source of radiation and one or more radiation-sensitive detector panels as well as the strobe-like quality of an intermittently pulsed radiation source and/or one or more intermittently-activated or reset radiation detector panels and/or intermittently processed data from said detector panels. Utilizing this technique reduces the effect of overlapping layers.

BRIEF DESCRIPTION OF THE DRAWINGS

The present invention will now be described in connection with one or more drawings, in which.

DETAILED DESCRIPTION

Figure 1A:
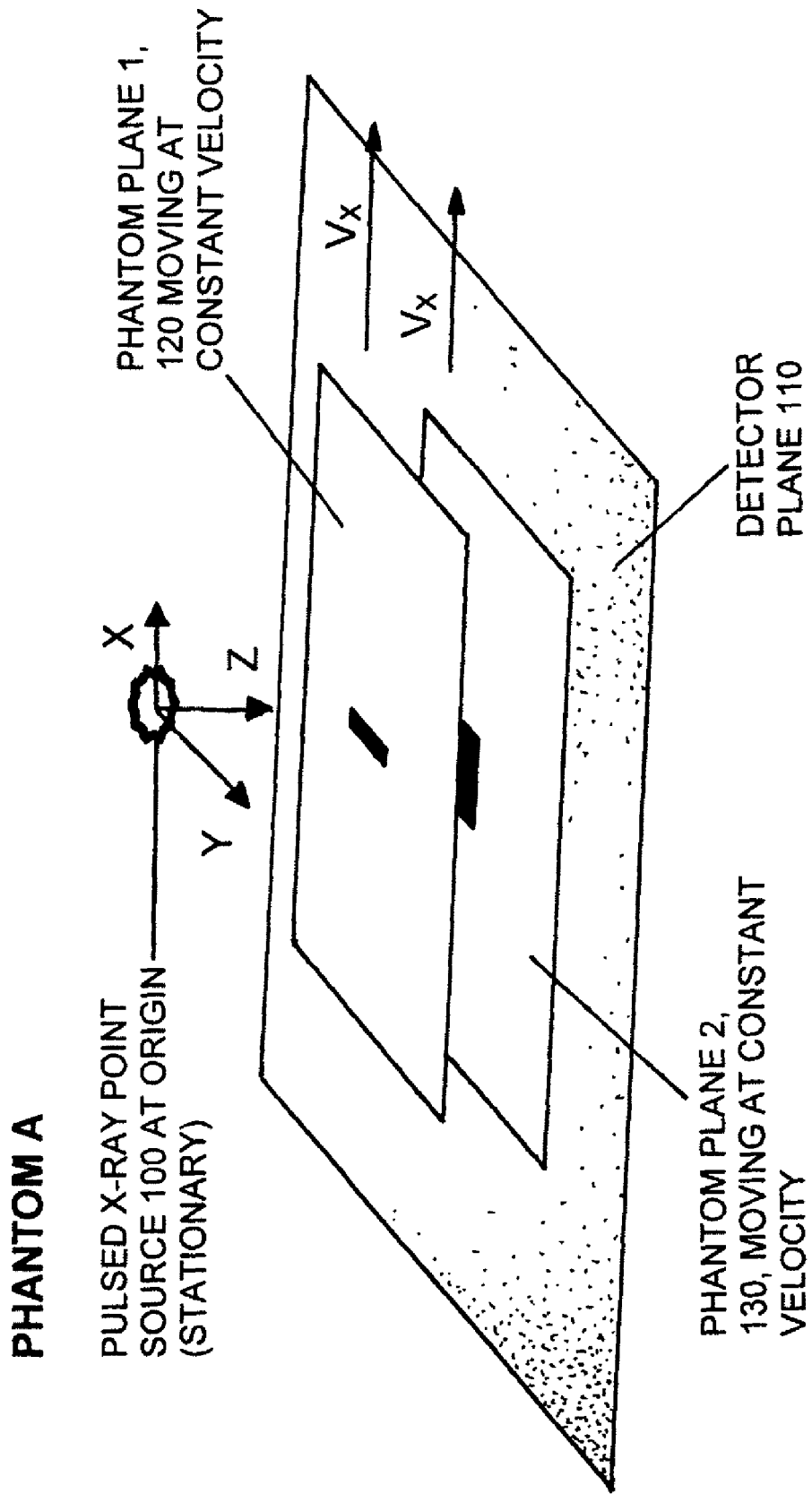
FIGS. 1A and 1B illustrate simulations of phantom experiments. A phantom is a test object used in imaging experiments. The reconstruction technique utilized in conjunction with at least one disclosed embodiment is illustrated in subsequent figures.

The present invention will now be described in connection with one or more contemplated embodiments. The embodiments discussed are not intended to be limiting of the scope of the present invention. To the contrary, the embodiments described herein are intended to be exemplary of the broad scope of the present invention. In addition, those skilled in the art will appreciate certain variations and equivalents of the embodiments described herein. The present invention is intended to encompass those equivalents and variations as well.

Various individuals have done work in optical cameras with pseudo randomly-activated shutter-acquired images that can be de-blurred mathematically. See, for example, R. Raskar, A. Agrawal, J. Tumblin, *Coded Exposure Photography: Motion Deblurring using Fluttered Shutter*, ACM Transactions on Graphics (TOG), 25(3):795-804 (2006) (hereby incorporated by reference in its entirety).

Disclosed embodiments provide an apparatus and a method that perform an image reconstruction technique that takes advantage of an object's linear translation between a radiation source and radiation-sensitive detector panels. It is understood that the term "panel" implies hardware capable of converting two- or three-dimensional x-ray flux that is impinging on the panel into signals that can eventually be processed by a computer. Examples of such a panel include an array of x-ray detector pixels (i.e., PIN diodes), each of which will provide an electrical signal that is simplified and sent to a computer for processing, or an array of optically-sensitive detector elements (e.g., silicon photomultipliers) placed in optical contact with a scintillating layer that converts x-rays to light.

It is understood that the type of radiation emitted by the source may be x-rays or other forms of electromagnetic or particulate radiation, for example gamma-rays or neutrons.

Utilizing the above method and apparatus reduces the effect of overlapping layers. It is understood that the translation required in the method and apparatus can be relative, i.e., effected by moving the object, or alternatively by moving the source, or by utilizing multiple sources at different locations that fire at different times, thereby creating the effect of source motion. Alternatively, both the source and object can be moved.

It is understood that the translation can be linear or angular or a combination of both linear and angular. Alternatively, an x-ray source that is in motion but is not pulsed can have the pulsation simulated by turning the x-ray detector on and off or by separately examining frames of data collected by the x-ray detector at different times.

Simulations to determine the feasibility of such an apparatus and method have been performed using a software package (MATLAB) to simulate various x-ray acquisition geometries. Initial simulations relied on an assumption that there is no statistical noise (i.e., there are an infinite number of x-ray photons per exposure). With that assumption in place, simulations were performed using a plurality of phantoms, i.e., objects in various imaging techniques used to visualize or enhance visualization by simulating conditions encountered in a procedure. As is conventionally known, phantoms may be used in procedures employing or measuring x-irradiation or radioactive material to evaluate performance. Thus, simulations involving mathematical data denoting such phantoms were used.

Data associated with two types of phantoms was used in the simulations (FIGS. 1A and 1B); each set of phantom data consisted of two parallel sheets of data points with varying attenuation patterns. In both cases, the phantoms data was simulated as moving at constant velocity with respect to fixed sources and detectors.

As illustrated in connection with FIGS. 1A and 1B, for purposes of simulation, the (point) source of pulsed x-rays was located at the origin of the axes. The plane of the detector was located at Z=50 mm, with X dimension of 200 mm and Y dimension of 100 mm with 0.5 mm/pixel. The phantom was a three-dimensional object represented by two planes (40 mm×40 mm in size) parallel to the detector plane. Planes 1 and 2 were located at Z=20 mm and Z=40 mm respectively. In Phantom A, the pattern for plane 1 (120) consisted of an opaque rectangle (transparency 1, measuring 1 by 5 mm) on a background with transparency 0.1, oriented along the y-axis. The rectangle in plane 2 (130) was oriented along the x-axis. In Phantom B, plane 1 (120) contains a set of concentric circles, and plane 2 (130) contains a combination of text and shapes.

The simulation translated the phantom in the x-direction, in order to simulate constant linear velocity with respect to the source and detectors. Projection of the phantom to the detector plane was simulated by tracing imaginary lines from the point source 100 to each pixel of the detector plane 110. Total attenuation along the traced line from the source 100 to corresponding detector pixel i was calculated as the sum of attenuation on each plane (j) according to (1):

$$S_i = \sum_{j=1}^{n} a_j \tag{1}$$

where $a_j$ is the attenuation for the pixel j of the phantom along the line from the X-ray source to detector pixel i. The x-ray intensity at detector pixel i is given by $I_i = e^{-S_i}$.

Projection images were calculated for x-ray pulse sequences in two methods, corresponding to either strobe or blur mode. In strobe mode, short x-ray pulses at the beginning of each of n (e.g., six) steps were simulated along the phantom's path, resetting the detector plane between steps so that the images from one pulse did not interfere with the next. Thus, the intermittent quality of the source exposure may be effected by pulsing the source, or by turning the x-ray detector panel on or off, or by processing data sets collected from the detector panel so that each data set corresponds to a finite time duration. As in a strobe light, the projections were not blurred by motion. In the blur mode, n (e.g., 156) pseudo-random x-ray pulses were simulated across the phantom's path, with the detector reset every p (e.g., 26) pulses. In the blur case, a de-blurring algorithm may be applied that takes advantage of the preservation of spatial frequencies that occurs with coded pseudo-random exposures. See, Raskar et al. supra.

In both the strobe and motion-blurred cases, recovery of z-information about the phantom was attempted (i.e., to separate features from the two overlapping phantom planes) through back-projection and reconstruction methods. In order to cover the entire area of the phantom, the path of motion (and detector length) was twice the length of the phantom.

For back-projection, from each detector array pixel an imaginary line was drawn to the x-ray source. An attenuation value a was calculated from pixel intensity value I as $a=-\ln(I)$ and added to the intersection of this line with each phantom plane. For reconstruction, a simplified version of a Maximum Likelihood Expectation Maximization (MLEM)-like algorithm was used. Generally, an MLEM algorithm is as follows:

$$\lambda_j^{k+1} = \frac{\lambda_j^k}{\sum_i^m C_{ij}} \sum_i^m \frac{C_{ij} y_i}{\sum_j^m C_{ij} \lambda_j^k} \tag{2}$$

where $\lambda_j^k$ is the value of reconstructed image at the pixel j for the k-th iteration, $y_i$ is the measured projection data at i-th detector's bin, and $C_{ij}$ is the detection probability that give the fraction of photons from pixel j to projection bin i. The value of $C_{ij}$ represents as the overlapped area between i-th ray tube and pixel j. Assumptions include that $C_{ij}=1$ for any i,j that belong to the same line from point source to detector pixel i, and $C_{ij}=0$ for all other combinations of i and j. Normally MLEM is used for emission processes (e.g., PET or SPECT) in which case the detector values are proportional to the sum of image values. In case of x-ray detectors, whose values depend exponentially on the sum of image values, the reconstruction was applied to the logarithm of the intensity measured at each detector pixel:

$$y_i = -\ln(I_i) = S_i = \sum_j a_j \tag{3}$$

Results of strobe simulation experiments are shown in FIG. 2. As illustrated in connection with that figure, the reconstruction process is able to recover three-dimensional information in both phantoms more accurately than simple back-projection. More specifically, Back-projected (top) and reconstructed (bottom) images at slices with z-positions 20 mm and 40 mm are shown for the simple rectangular phantom of FIG. 1A (on left) and for the complex phantom of FIG. 1B (on right). As should be apparent from FIG. 2, the reconstructed images are able to recover the three dimensional information of the phantom much better than the back-projected images.

Figure 1B:
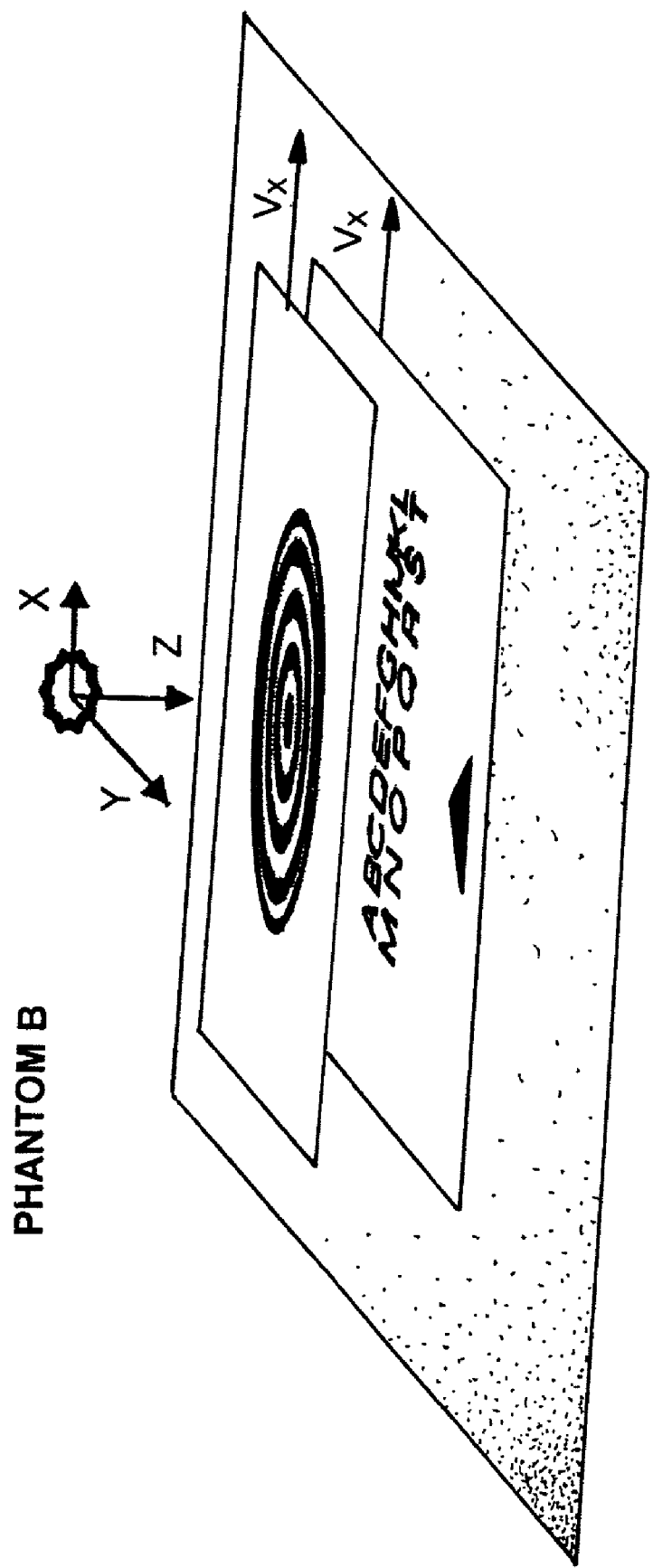
Figure 2A:
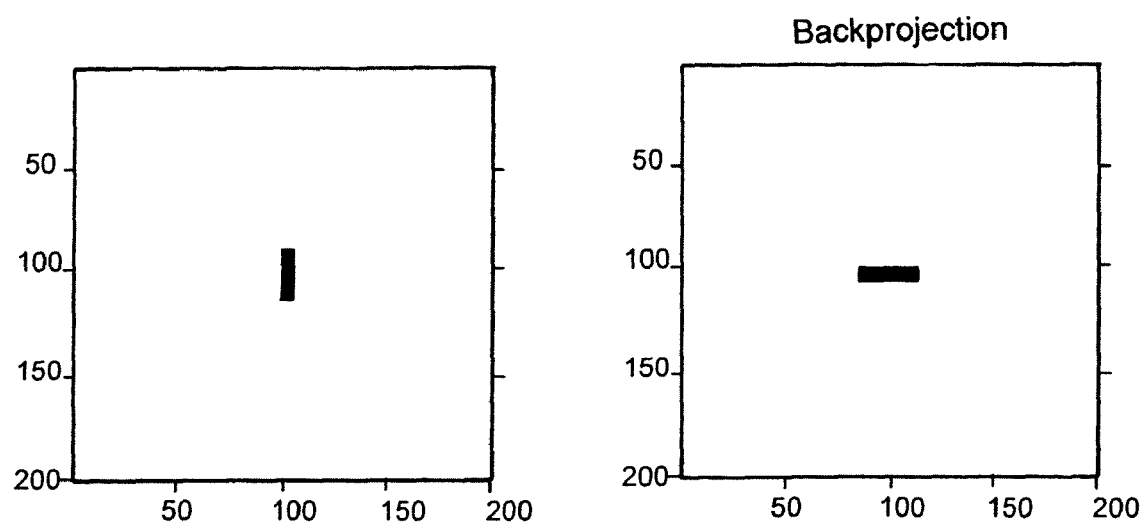
FIG. 2 illustrates results of strobe simulation experiments for a device designed in accordance with at least one disclosed embodiment.
Figure 2B:
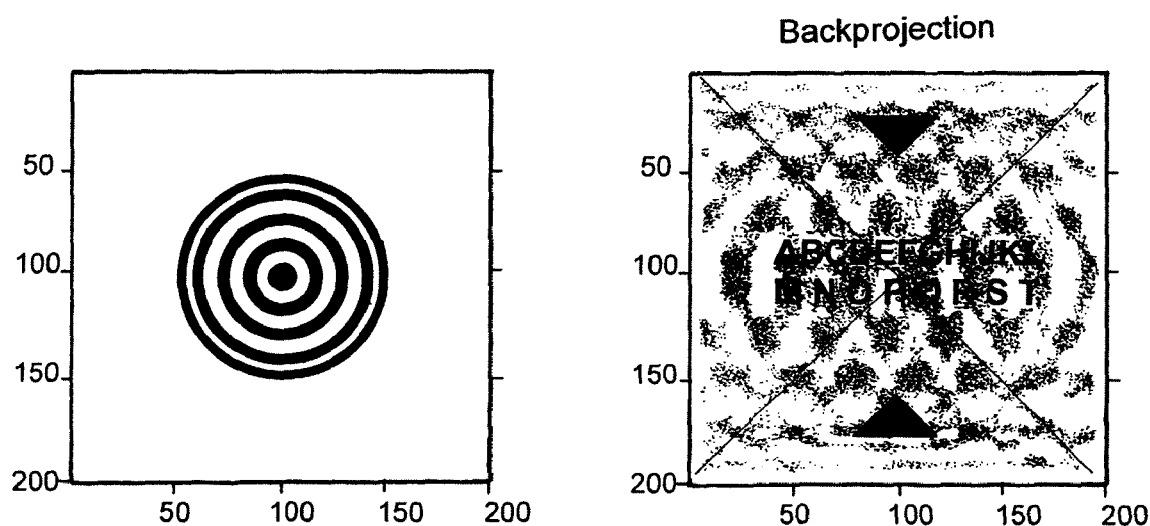
Figure 2C:
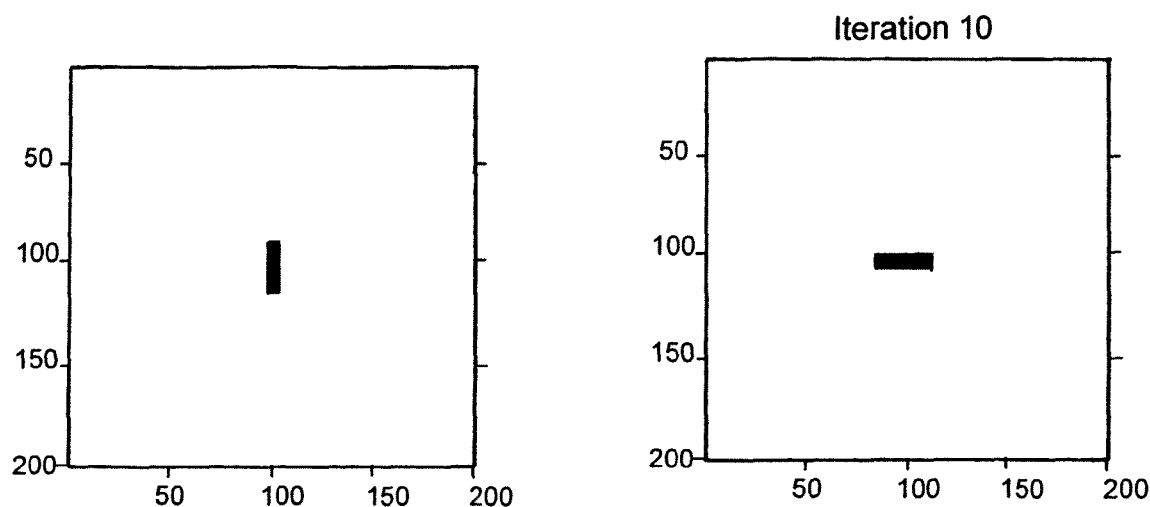
Figure 2D:
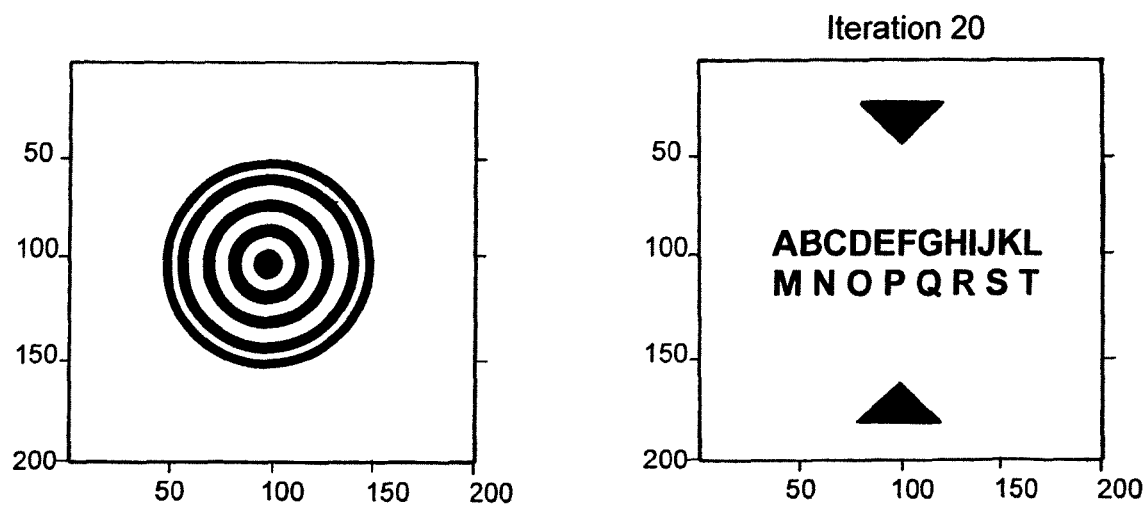
Figure 3A:
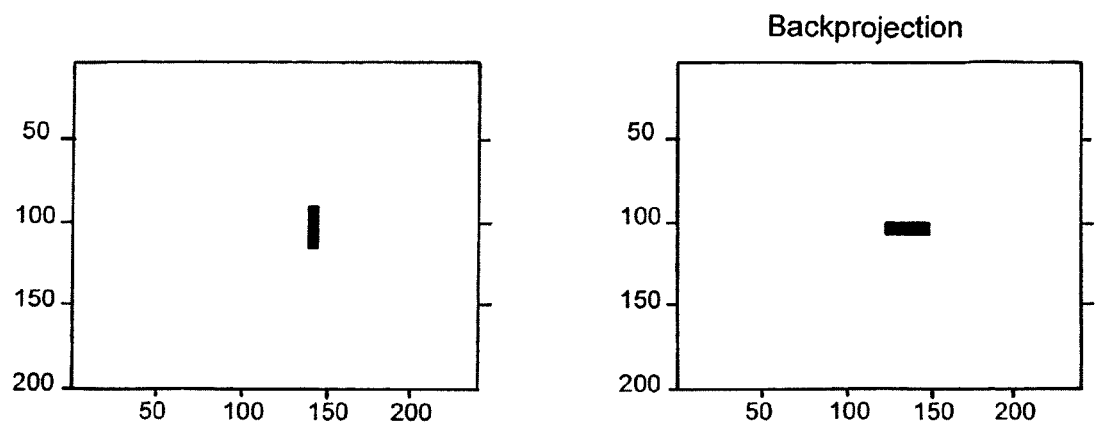
FIGS. 3A-D illustrate back-projected (top) and reconstructed (bottom) images for the simple rectangular phantom of FIG. 1A (on left) and for the complex phantom of FIG. 1B (on right).
Figure 3B:
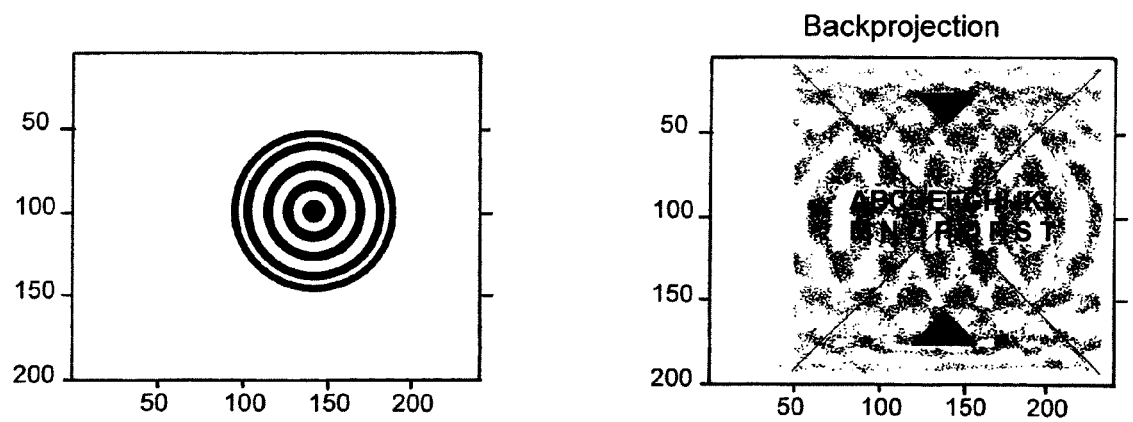
Figure 3C:
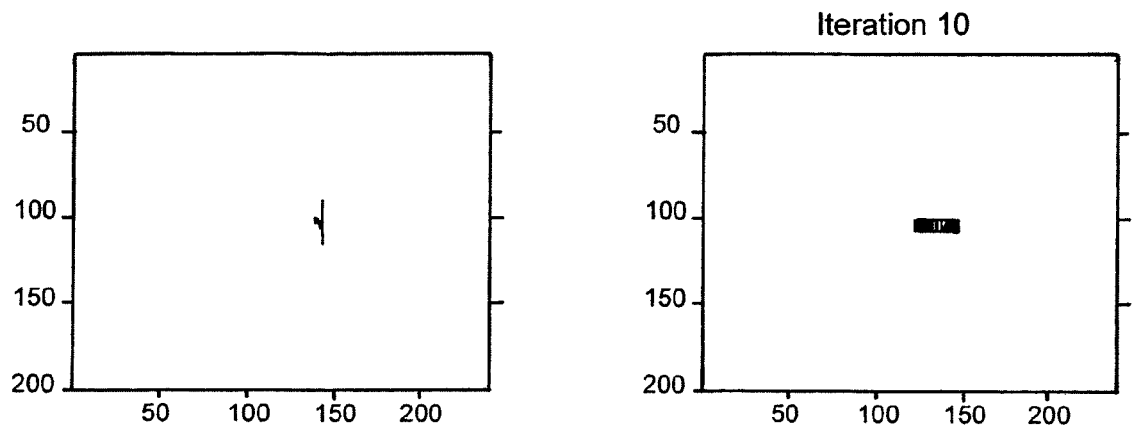
Figure 3D:
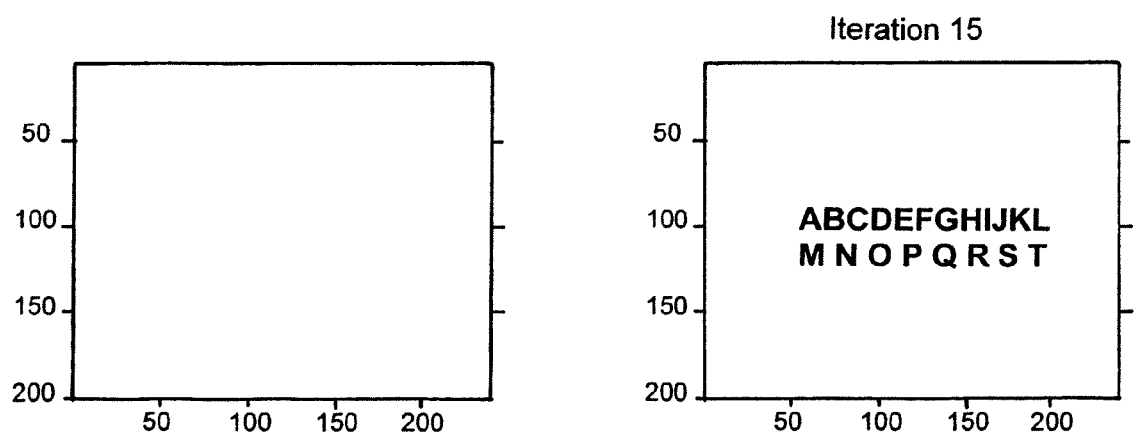

As illustrated in FIGS. 3A-D, back-projected (top) and reconstructed (bottom) images are shown for the simple rectangular phantom of FIG. 1A (on left) and for the complex phantom of FIG. 1B (on right). However, as shown in those figures, the reconstructed images are able to remove the effect of overlapping planes only slightly better than the back-projected images.

Thus, although laminography and tomosynthesis methods have long been used in medical imaging and homeland security applications, the use of pulsed imaging (whether implemented at the source, the detector, or in data frame analysis) may improve three-dimensional visualization without adding significant cost or complexity to an imaging apparatus. This advantage further adds to the noise-reduction properties for pulsed x-rays that are conventionally known. See, for example, G. Cao, Y. Z. Lee, R. Peng, Z. Liu, R. Rajaram, X. Calderon-Colon, L. An, P. Wang, T. Phan, S. Sultana, D. S. Lalush, J. P. Lu, O. Zhou, *A dynamic micro-CT scanner based on a carbon nanotube field emission x-ray source*, Phys. Med. Biol., 54:2323-2340 (2009) (hereby incorporated by reference in its entirety).

Thus, the use of intermittent x-ray exposures can be combined with various different conventionally known image data reconstruction methods to improve three-dimensional visualization of linearly-moving objects. A strobe effect, utilized to provide this intermittent x-ray exposure, can be implemented by pulsing the x-ray source and/or by blanking a receptor intermittently and/or by processing the data collected from a receptor to achieve such an intermittent effect.

Alternatively, instead of moving the object of interest, the strobe effect may be implemented by moving the source and receptor linearly with respect to a fixed object. As an example, the object can be a compressed breast, and an x-ray source (or other source of radiation) and the receptor may be moved linearly with respect to the fixed breast, or the x-ray source can move linearly with respect to a fixed breast and fixed receptor. Again, the source may be pulsed or the detector may be intermittently reset, or both may occur, in order to achieve the intended improvement in reconstruction quality.

Thus, it should be understood that linear motion can include other types of motion which are linear for a portion of the time, which includes almost all types of motion when examined with high temporal resolution.

Figure 4:
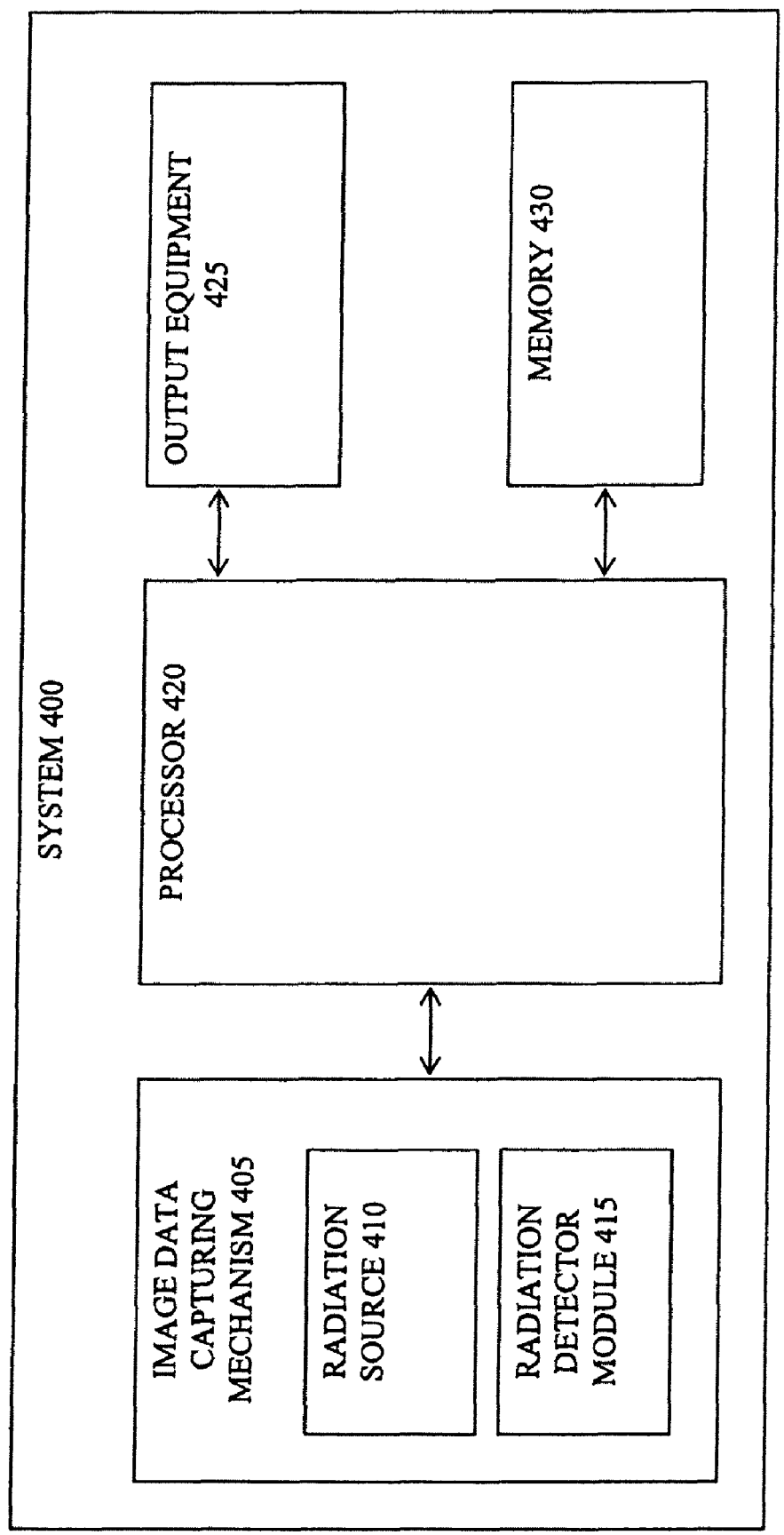
FIG. 4 illustrates a device designed in accordance with the principles of at least one disclosed embodiment.

FIG. 4 illustrates one example of an apparatus that may be designed or operated in accordance with the disclosed embodiments. As shown in FIG. 4, the system 400 may include an image data capturing mechanism 405 that may include both a radiation source 410 and a radiation detector module 415 that may include, among other things, one or more radiation-sensitive detector panels configured to detect particles emitted from the radiation source 410. The image data capturing mechanism 405 is coupled to a processor 420 that may be configured to run software to both control operation of the image data capturing mechanism 405 as well as perform intermittent collection or processing of the image data from the at least one radiation-sensitive detector panel(s).

Likewise, the processor 420 may be configured to run a computed tomography algorithm, as disclosed herein, to reduce the effect of overlapping layers in images of the object being imaged. The processor 420 may be further configured to output the image data and/or one or more graphical or image representations of the data to output equipment 425. That output equipment 425 may include, for example, one or more computer screens, printers, etc. provided to enable review of that output data by medical and diagnostic personnel. It should be understood that the link between the processor 420 and the output equipment may be a wired link, a wireless transmission medium or any other direct or indirect connection that enables transfer of data.

Likewise, the processor 420 may be further configured to output the image data and/or one or more graphical or image representations of the data to memory 430 for storage and further analysis or reference at a later date. Further, the software code, instructions and algorithms utilized by the processor 420 may be stored in the memory 430. Accordingly, memory 430 may include any type of known memory device including any mechanism for storing computer executable instructions and data used by a processor. Further, the memory may be implemented with any combination of read only memory modules or random access memory modules, optionally including both volatile and nonvolatile memory. Alternatively, some or all of the device computer executable instructions may be embodied in hardware or firmware (not illustrated).

Further, it should be appreciated that, although not illustrated, the system 400 may include one or more user interfaces that may include display screens, one or more keyboards, and other types of user interface equipment.

As noted above, there are numerous variations and equivalents of the present invention that should be appreciated by those skilled in the art. The present invention is intended to encompass those equivalents and variations.

What is claimed is:

1. A device for performing image reconstruction of an object of interest, the device comprising:
    at least one source of radiation configured to operate as an emitter of particles for imaging; and
    at least one radiation-sensitive detector panel configured to operate as a detector of particles emitted from the at least one source of radiation, wherein there is at least occasional relative motion between either the at least one source of radiation or the object of interest or the at least one radiation-sensitive detector panel;
    at least one processor configured to collect data from the at least one radiation-sensitive detector to implement intermittent collection of data from the at least one radiation-sensitive detector panel; and
    a computed tomography algorithm module running on the at least one processor and configured to reduce the effect of overlapping layers in images of the object of interest resulting from processing of the data from the at least one radiation-sensitive detector panel,
    wherein the at least one source of radiation is configured to operate in pulsed mode to achieve intermittent collection of data from the at least one radiation-sensitive detector.

2. The device of claim 1, wherein the at least one radiation-sensitive detector panel is configured to operate in an intermittently-blanked mode to achieve intermittent collection of data from the radiation-sensitive detector.

3. The device of claim 1, wherein the data collected from the at least radiation-sensitive detector panel is configured into sets to simulate intermittent collection of data from the radiation-sensitive detector.

4. The device of claim 1, wherein the relative motion of the object of interest with respect to the source of radiation or the radiation-sensitive detector panel is at least part-wise linear.

5. The device of claim 1, wherein the relative motion of the object of interest with respect to the source of radiation or the radiation-sensitive detector panel is at least part-wise angular.

6. The device of claim 1, wherein the computed tomography algorithm is further configured to perform computed tomography through image reconstruction of a data set containing projections obtained at angles on one or more sides of the object of interest.

7. The device of claim 1, wherein the computed tomography algorithm is further configured to perform computed tomography through image reconstruction of a data set containing projections obtained at angles on one or more sides of the object of interest.

8. The method of claim 7, wherein the at least one radiation-sensitive detector panel is configured to operate in an intermittently-blanked mode to achieve intermittent collection of data from the radiation-sensitive detector.

9. The method of claim 7, wherein the data collected from the at least radiation-sensitive detector panel is configured into sets to simulate intermittent collection of data from the radiation-sensitive detector.

10. The method of claim 7, wherein the relative motion of the object of interest with respect to the source of radiation or the radiation-sensitive detector panel is at least part-wise linear.

11. The method of claim 7, wherein the relative motion of the object of interest with respect to the source of radiation or the radiation-sensitive detector panel is at least part-wise angular.

12. The method of claim 7, wherein the computed tomography algorithm is further configured to perform computed tomography through image reconstruction of a data set containing projections obtained at angles on one or more sides of the object of interest.

13. A method of performing image reconstruction of an object of interest, the method comprising:
    emitting particles from at least one radiation source for imaging from the at least one source of radiation; and
    detecting the particles emitted from the at least one source of radiation by at least one radiation-sensitive detector panel, wherein there is at least occasional relative motion between either the at least one source of radiation or the object of interest or the at least one radiation-sensitive detector panel;
    performing intermittent collection of data from the at least one radiation-sensitive detector panel regarding the detected particles emitted from the at least one source of radiation; and
    performing computed tomography on intermittently collected or processed data to reduce the effect of overlapping layers in images of the object of interest,
    wherein the at least one source of radiation is configured to operate in pulsed mode to achieve intermittent collection of data from the at least one radiation-sensitive detector.

* * * * *